United States Patent [19]

Alley

[11] 4,326,520
[45] Apr. 27, 1982

[54] BRAKE-ACTUATED CATHETER FEEDER

[76] Inventor: Ralph D. Alley, 13 Spring Street Rd., Loudonville, N.Y. 12211

[21] Appl. No.: 218,497

[22] Filed: Dec. 22, 1980

Related U.S. Application Data

[63] Continuation of Ser. No. 17,540, Mar. 5, 1979, abandoned.

[51] Int. Cl.³ .............................................. A61M 5/00
[52] U.S. Cl. .................................................. 128/214.4
[58] Field of Search ................ 128/214 R, 214.4, 221, 128/347–350, DIG. 9, DIG. 16

[56] References Cited

U.S. PATENT DOCUMENTS

| | | | |
|---|---|---|---|
| 3,515,137 | 6/1970 | Santomieri | 128/214.4 |
| 3,561,445 | 2/1971 | Katerndahl et al. | 128/214.4 |
| 3,610,240 | 10/1971 | Harautuneian | 128/214.4 |
| 3,633,579 | 1/1972 | Alley et al. | 128/214.4 |
| 3,682,173 | 8/1972 | Center | 128/214.4 |
| 3,825,001 | 7/1974 | Bennet et al. | 128/214.4 |
| 3,835,854 | 9/1974 | Jewett | 128/214.4 |
| 3,861,395 | 1/1975 | Taniguchi | 128/349 R |
| 4,006,744 | 2/1977 | Steer | 128/214 R |
| 4,037,600 | 7/1977 | Poncy et al. | 128/214.4 |

Primary Examiner—C. Fred Rosenbaum
Attorney, Agent, or Firm—Wegner, Stellman, McCord, Wood & Dalton

[57] ABSTRACT

A catheter feeder is comprised of two parts that are secured together about a catheter as the catheter is being inserted into a vessel, such as a vein or artery in a cardiovascular system. The catheter feeder is provided with a finger-operated brake. The catheter feeder encircles a portion of the length of the catheter and has a protrusion adapted to be received by the open proximal end of an introducer cannula. Concentrically disposed about the catheter is a ferrule which has a distal portion also received within the catheter feeder. A sterile sleeve or sheath encloses the catheter and ferrule and has a collar engaging with the catheter feeder to hold the two parts thereof assembled. The brake engages the ferrule to compress one end thereof into a locking position about the catheter. When the brake is disengaged, the catheter can be manipulated through the catheter feeder and when the brake is engaged, the sterile sleeve or sheath is combed back relative to the catheter. When the catheter has been threaded to the selected location, the protrusion is removed from the introducer cannula and the collar on the sterile sheath is removed from the catheter feeder whereupon the two parts of the catheter feeder are separated and dropped from the catheter. The ferrule is then wedged into the introducer cannula for retaining the catheter at the selected location.

14 Claims, 10 Drawing Figures

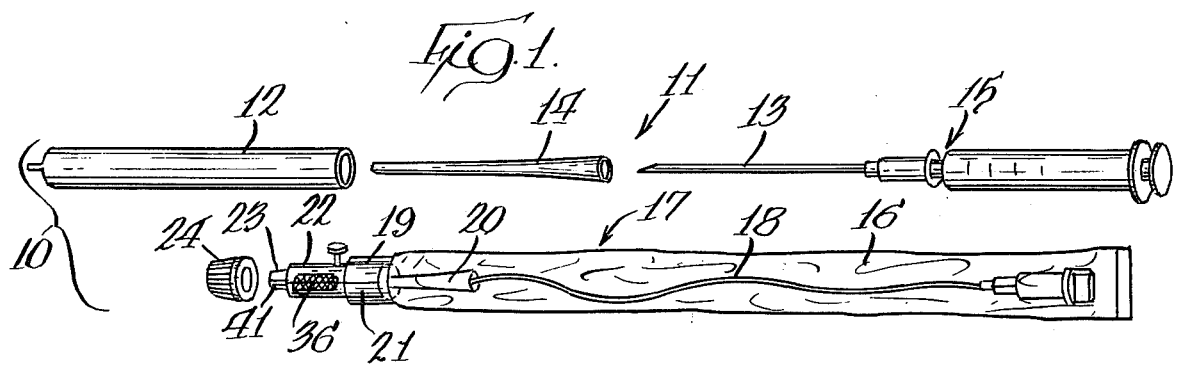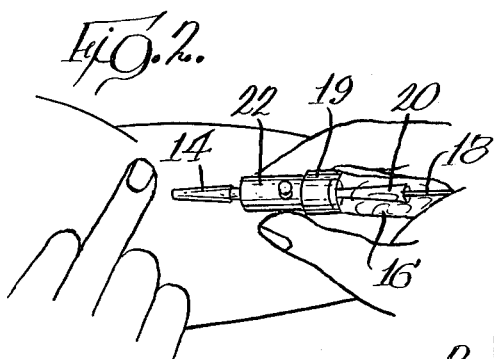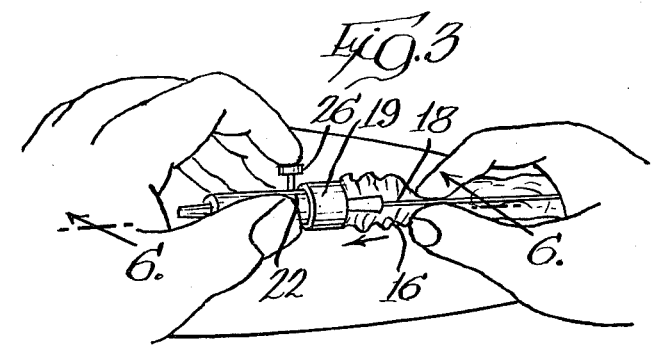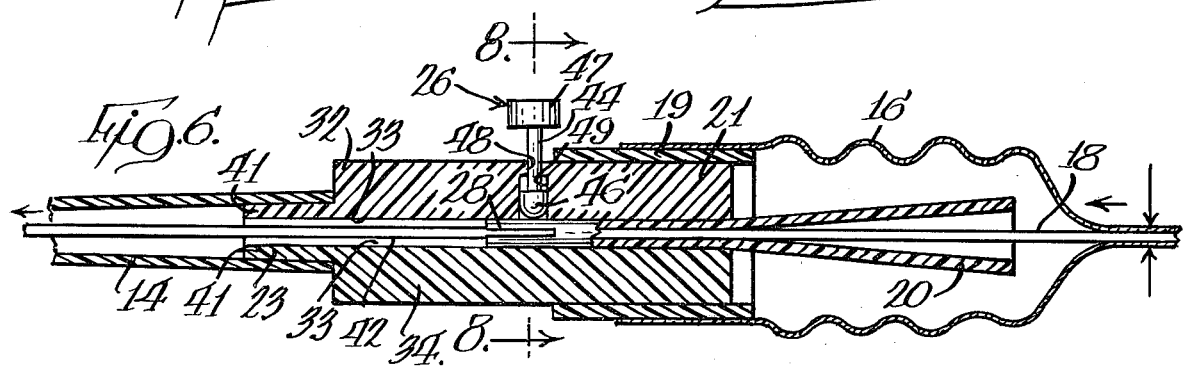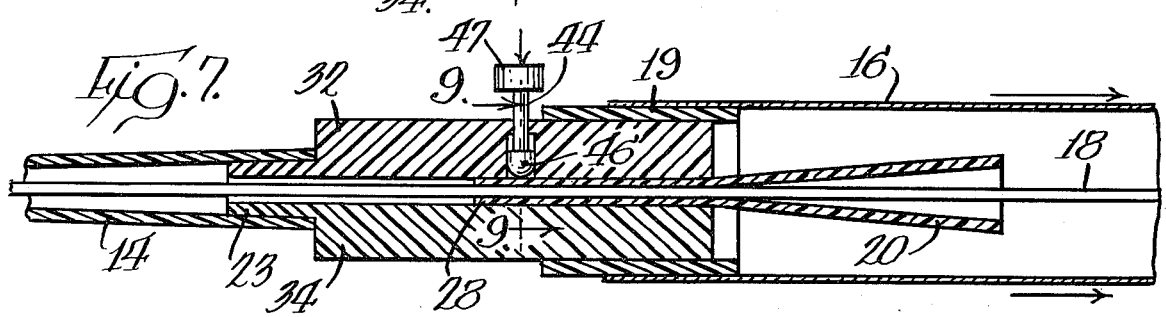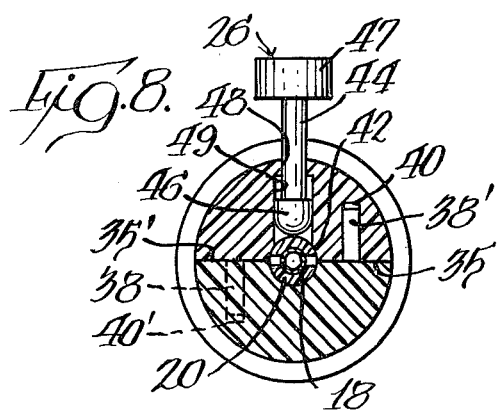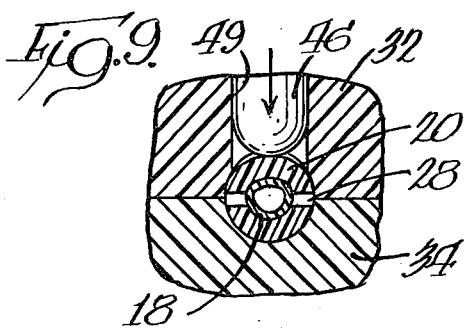

BRAKE-ACTUATED CATHETER FEEDER

This is a continuation of application Ser. No. 17,540, filed Mar. 5, 1979, now abandoned.

BACKGROUND OF THE INVENTION

1. Field of the Invention

This invention relates to a catheter assembly and, more particularly, to a catheter feeder for manipulating the catheter, as during feeding of the catheter into a vein or artery of a patient through an indwelling introducer cannula.

2. Description of the Prior Art

Disposable sterilized catheters for use in the cardiovascular system of humans and laboratory animals have long been known to the prior art. Briefly, the catheter assemblies include a syringe, a needle and an introducer cannula together with a catheter of a suitable length upon which a freely movable ferrule rides with the catheter disposed within a sanitary protective sleeve or sheath. The sleeve or sheath is provided with a cap which is removed prior to use. The physician implants the introducer cannula in the patient by use of the syringe and needle. The cap is removed from the sanitary sleeve and the catheter is threaded through the introducer cannula into the patient. The catheter is manipulated by the physician through the sanitary sleeve wherein the catheter is urged forward, is gripped through the distal part of the sleeve as the sleeve is combed back relative to the catheter, and is again urged forward to acquire the appropriate placement in the vein or artery at a desired location. When the particular location of the catheter is achieved, the ferrule is wedged in the introducer cannula to provide an interference fit therebetween to lock the catheter at the desired location. The other end of the catheter, having a connector, is thereafter used either by coupling to intravenous equipment, to pressure recording equipment, to an electronic sensing device, or by other applications known to the art.

Two serious drawbacks are present in this type of a catheter system. Specifically, digitally squeezing the sleeve to grip the catheter so that the sleeve can be combed back to free up more catheter for threading into the vein or artery is awkward. Moreover, many of the feeders known to the prior art have not recognized the advantages of providing a catheter feeder which is removable from the catheter after it has been placed at a selected location.

SUMMARY OF THE INVENTION

A catheter feeder is provided as a part of a catheter assembly for use in cardiovascular systems of humans and laboratory animals. The feeder includes a barrel-shaped element formed of similarly shaped parts wherein a bore extends through the feeder for receiving the catheter. The feeder aids in threading the catheter and is removable from the catheter by separating the parts of the barrel-shaped element. A finger-operated brake is provided on one of the parts of the element for either engaging or disengaging the catheter by pressure transmitted through an interposed overlying pad or ferrule during feeding of the catheter. After the parts have been removed, the ferrule may be advanced into a patient implanted introducer cannula for retaining the catheter at a desired location.

It is a feature of the present invention to provide a catheter assembly having an improved catheter feeder.

It is another feature of the present invention to provide a catheter feeder that is removable from the catheter after the catheter has been placed at a desired location within the patient.

Another feature of the invention is that the assembly provides a "closed system" so that gloves are not needed for aseptic insertion of the catheter, a feature that fulfills contemporary practice standards.

And still another feature of the present invention is to provide a catheter feeder which is removable from the catheter by separating the parts of the feeder and permitting the parts to fall free. The catheter feeder has a brake to facilitate controlled, alternating prograde or retrograde threading of the catheter within a blood vessel with equal ease. This versatility of manipulation is often necessary in catheterizing a vein wherein the tip of the catheter may get stuck, for example, by impingement on tributary branches or venous valves.

These and other features of the invention will become apparent when considering the drawing in combination with the detailed description that follows.

BRIEF DESCRIPTION OF THE DRAWINGS

FIG. 1 is a diagramatic view of the catheter assembly in accordance with the present invention;

FIG. 2 is a perspective view of the catheter feeder being manipulated by the physician to insert the catheter into the cannula;

FIG. 3 is a perspective view of the catheter feeder being manipulated by the physician during introduction of the catheter into a patient;

FIG. 6 is a cross-sectional view of the catheter assembly taken through the line 6—6 in FIG. 3 depicting a finger-operated brake disengaged and the catheter being fed through the catheter feeder;

FIG. 7 is a cross-sectional view similar to FIG. 6 depicting the finger-operated brake engaged and the sanitary sleeve being returned or combed back to its original position;

FIG. 8 is a cross-sectional view taken through the line 8—8 in FIG. 6;

FIG. 9 is a detailed cross-sectional view of the brake engaging a locking ferrule and catheter.

DESCRIPTION OF THE PREFERRED EMBODIMENT

Figure 4:
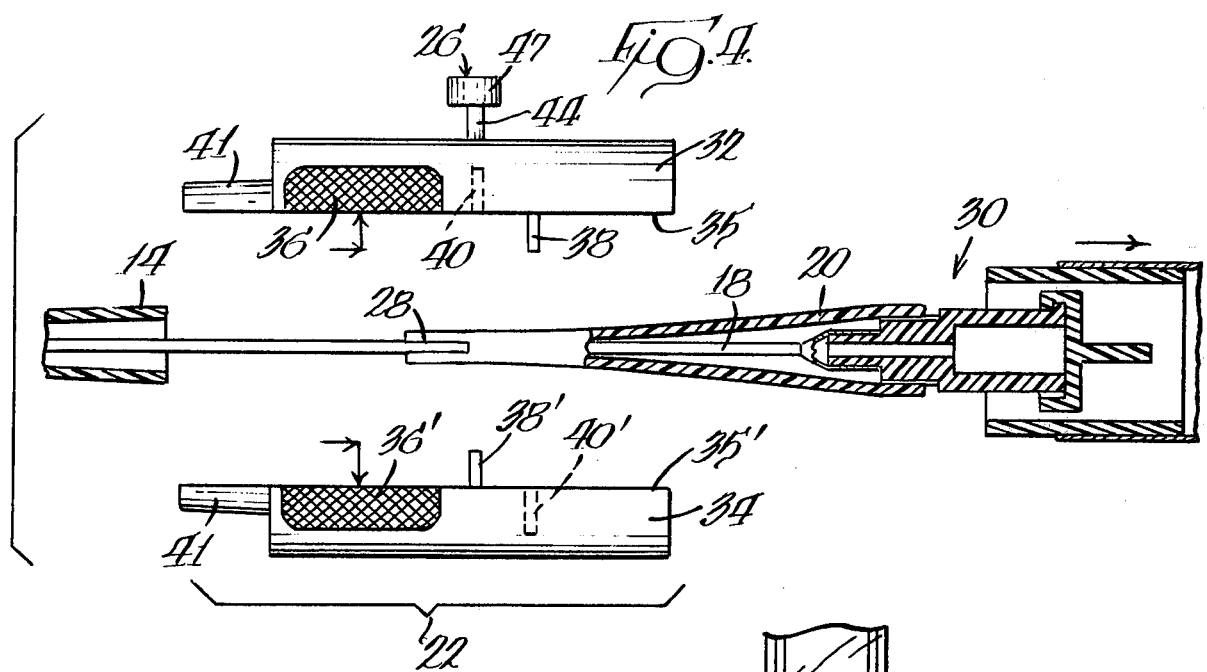
FIG. 4 is an exploded perspective view, partly in cross section, showing the catheter feeder being removed from the catheter.

Referring to FIG. 1, the catheter assembly 10 is made up of two units 11 and 17. One unit 11 is shown exploded apart and includes a needle sheath 12, a cannula introducer 14, and a needle 13 of a syringe and needle assembly 15. Unit 11 is normally delivered with the needle sheath 12 telescoped over the cannula introducer 14 which encircles a needle 13 of the syringe and needle assembly 15. The second unit 17 is shown to include a protective sanitary envelope or sleeve 16 encasing both a catheter 18 and a ferrule 20, and has a collar 19 engaging around one end portion 21 of an improved catheter feeder 22 with the other end portion 23 of the catheter feeder being positioned in a protective cap 24. Catheter 18 is well suited for many applications within the cardiovascular system, but will be described for use particularly for intravenous infusions to illustrate the versatility of the catheter feeder.

Referring to FIGS. 1-3, the sheath 12 is removed from the cannula 14 and needle 13 of the syringe and needle assembly 15. Needle 13 and cannula 14 are implanted in a vessel in a patient by the use of the syringe and needle assembly 15 which is then aspirated to ensure that the cannula 14 is appropriately positioned, for instance, within a vein. The needle and syringe assembly 15 is then removed from the cannula 14 whereupon back flow of blood through the cannula is arrested either by inserting a plug in the proximal end of the cannula or by the physician applying finger pressure to the vein to obstruct the distal, intravenous end of the cannular. In FIG. 2, the physician's finger is being applied to the patient's vein to shut off the flow of blood to the cannula. Protective cap 24 is removed from end portion 23 of the catheter feeder 22 and said end portion 23 of the catheter feeder is seated in the open end of the cannula 14 with the end of the catheter 18 being threaded into said cannula 14.

As shown in FIG. 2, the feeder 22 is wedged into said cannula 14 by pressing the two axially together and, in some cases, giving a slight twist to one relative to the other. The physician manipulates catheter 18 into the vein by grasping catheter feeder 22 in one hand (i.e. as shown in FIG. 3, the left hand) and by gripping catheter 18, through sanitary sleeve 16, in the right hand at a location spaced from the feeder (i.e. such as one or two inches from the feeder). Specifically, as best seen in FIG. 3, catheter 18 is gripped and urged into the cannula 14 in the direction shown as the sanitary sleeve 16 is bunched up between the fingers of the physician and the end portion 21 of the catheter feeder 22. When the physician's fingers reach the rear portion of the catheter feeder 22, a finger-operated brake 26 carried by the feeder 22 is depressed to arrest movement of the catheter 18. The grip on the catheter 18 through the sleeve 16 is released whereupon the protective sanitary sleeve 16 is combed back or returned to its position as shown in FIG. 1. This process (which is illustratively depicted in FIGS. 6-7) is repeated until catheter 18 is in position in the patient at the desired location. Catheter 18 can be moved to work past obstructions, venous valves, angles, or withdrawal if the catheter enters a tributary of the vein being catheterized. For example, frequently a catheter introduced through a forearm vein (brachial vein) intended to lie in the superior vena cava to measure central venous pressure (CVP) will enter the internal jugular vein and be directed toward cerebral circulation instead of going downstream to the superior vena cava.

Figure 5:
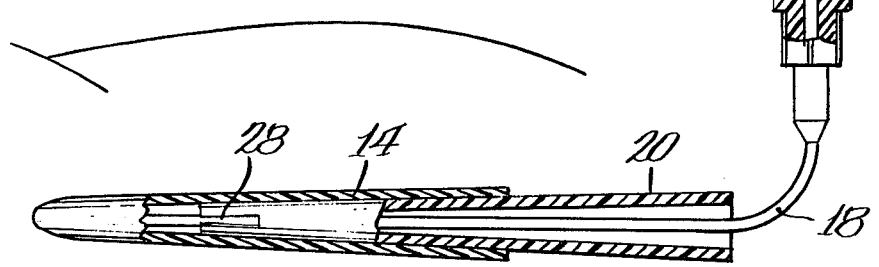
FIG. 5 is a perspective view of the catheter assembly, partly in cross section, with the catheter retained in place by a patient implanted cannula and a ferrule.
Figure 10:
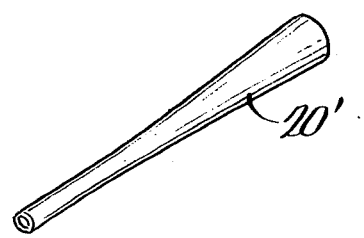
FIG. 10 is a perspective view of an alternative embodiment of the locking ferrule.

Referring to FIGS. 4 and 5, once the catheter 18 is properly positioned within the patient, the collar or ring 19 on the sanitary sleeve 16 is removed from the end portion 21 of the feeder 22 and the end portion 23 is removed from the cannula 14 whereupon the two parts 32 and 34 of the feeder 22 separate and are dropped from the catheter 18. The ferrule 20 is inserted into cannula 14 for retaining catheter 18 at the selected location. The distal end of the ferrule 20 is provided with a slit 28 that cooperates with an inner taper of cannula 14 to provide an interference fit at its end to capture and retain the catheter as best seen in FIG. 5 and as is covered by U.S. Pat. No. 3,633,579 in the names of Ralph D. Alley and David S. Sheridan, entitled Catheter Placement Device and Method. The sterile sleeve 16 is stripped from the catheter 18 with the proximal end of said catheter being coupled to intravenous equipment 30 and operated in the well known manner.

Referring to FIG. 4, and FIGS. 6-10, the construction of the improved catheter feeder 22 will now be described. Catheter feeder 22 is a barrel-shaped element or bivalve formed of similarly shaped first and second parts or halves 32 and 34 of molded plastic. The halves 32 and 34 may be provided with a flattened and knurled area 36 and 36' to facilitate the digital manipulation of the feeder 22. Each of the halves 32 and 34 is provided with a stud 38 and 38', respectively, along with a corresponding stud receptacle 40 and 40'. The studs 38, 38' and receptacles 40,40' cooperate to provide the alignment of the halves 32 and 34. The end portion 23 of the feeder 22 is comprised of a reduced diameter protrusion 41 formed integrally with and extending forward from the feeder 22. One half of the protrusion 41 is formed on half 32 and the other half is formed on half 34.

Each half 32 and 34 is provided with a channel 33 along mating surfaces 35 and 35' and when the halves 32 and 34 are properly aligned with studs 38,38' seated in receptacles 40,40', the channels 33,33 form a cylindrical bore 42 extending through the halves 32,34 and through the protrusion 41 for receiving catheter 18 and ferrule 20. The diameter of the bore 42 is sufficient to receive the end portion of the ferrule 20, as best in FIGS. 6 and 7, with the split end 28 of the ferrule 20 positioned in line with the brake 26. The ferrule 20, being tapered in length, expands the two halves 32,34 to urge the proximal end of the bivalve element 22 into wedged relationship with the ring or collar 19 to improve the sterile seal between the feeder 22 and the sleeve 16 and to more rigidly connect the feeder 22 to the sleeve 16. The ferrule 20 in the feeder 22 protects the catheter 18 from being deformed by the brake 26 particularly during storage and shipment of the catheter.

Finger-operated brake 26 is provided for selectively arresting and releasing the catheter 18 for prograde and retrograde movement relative to the feeder 22. The catheter 18 remains in a fixed position with respect to catheter feeder 22 when the brake 26 is engaged. Catheter 18 can be passed freely through the catheter feeder 22 and the ferrule 20 when brake 26 is disengaged. Brake 26 includes a rod 44 having on one end a rounded contact 46 and having on the other end an actuating handle 47. Rod 44 is slidably received in a reduced diameter opening 48 and the contact 46 is slidably received in an enlarged opening 49 with both openings 48,49 being in half 32 in transverse alignment with bore 42. As best seen in FIG. 9, pressure on the handle 47 urges the rod 44 downwardly causing the contact 46 to apply pressure to the split end 28 of the ferrule 20 and catheter 18. The ferrule 20 is made from a compressible material so that it will deform under pressure to grip the catheter and retain it in place relative to the feeder. The brake 26 can operate on any intermediate means, such as a pad that overlays the catheter between the brake and the catheter, which is capable of being urged against the catheter 18 to hold the catheter against movement relative to the element. Direct braking contact with the catheter, particularly when the catheter is soft or of delicate construction, may damage or deform the catheter.

The halves 32 and 34 may be retained together by any suitable means during use, however, a preferred form is illustrated and includes the semirigid plastic collar or ring 19 which is heat sealed, glued, or the like, on the open end of the sanitary sterile sleeve 16 and is interference fit over the end portion 21 of the two halves 32,34 to hold the two halves together. The collar or ring 19 would necessarily have a cross-sectional configuration corresponding to the cross-sectional configuration of catheter feeder 22.

Other alternate methods of maintaining the halves 32 and 34 together may also be desirable. For example, the size of the stud 38 and stud receptacle 40 may be selected to provide an interference fit for retaining the halves together or a band may be provided about the catheter feeder 22. Whatever method is used, it must be readily releasable so that the feeder 22 can be disassembled from the catheter with facility.

It is apparent that other ferrules may be suitable for use with the catheter feeder 22. For example, the ferrule 20', shown in FIG. 10, may be employed. Ferrule 20' does not have a slit in its end portion, but is of sufficient resilience that the brake 26 can distort it sufficiently to arrest movement of the catheter without undue pressure being required by the physician. It is also contemplated that a shoulder could be provided in the bore 42 in the feeder just forward of the location where the brake 26 enters the bore 42, so that the end of the ferrule 20,20' may abut thereagainst so as to positively position the ferrule in the proper position with respect to the brake 26.

The length of the feeder 22 is such that one hand of a physician can have a thumb and middle finger straddling the feeder with the index finger mainpulating the brake 26 while the other hand of the physician is free to thread the unbraked catheter prograde or retrograde, strip or comb the sterile sleeve 16 relative to the catheter 18 when the catheter is braked, and again advance or retract the catheter when the catheter is unbraked. Experts in the art will recognize that the catheter can be manipulated in a prograde or retrograde fashion with equal ease. The advantages of this versatility can be readily employed to manipulate the advancing catheter past obstructions, such as engagement of the catheter tip with venous valves or venous bifurcation spurs or to permit partial retraction of the catheter where the catheter has entered a tributary branch of the vein being catheterized.

I claim:

1. A device for aiding in threading a catheter for human or animal use, comprising:

an element formed from first and second similarly shaped parts and having a bore therethrough for receiving a catheter;

means for aligning said first and second parts;

independent means in said bore overlapping a portion of said catheter, said independent overlapping means is a ferrule concentrically disposed about the catheter;

brake means in said element for selectively urging said independent ferrule received within said bore between said brake means and said catheter into engaging and disengaging contact with said catheter so that when said brake means is engaged, said catheter remains in a fixed position with respect to said element, and when said brake means is disengaged, said catheter is able to pass freely in either direction through said bore; and means for retaining the first and second parts together.

2. The device of claim 1 wherein said element is removable from the catheter by separating said first and second similarly shaped parts.

3. A device for aiding in threading a catheter for human or animal use, comprising:

an element formed from first and second similarly shaped parts and having a bore therethrough for receiving a catheter;

means for aligning said first and second parts;

independent means in said bore overlapping a portion of said catheter;

brake means in said element for selectively urging said last-named independent means into engaging and disengaging contact with said catheter so that when said brake means is engaged, said catheter remains in a fixed position with respect to said element, and when said brake means is disengaged, said catheter is able to pass freely in either direction through said bore;

means for retaining the first and second parts together;

said means for retaining the parts together includes:

a sterile sleeve for receiving the catheter having an open end and a sealed end; and a ring secured to the sterile sleeve at the open end for receiving said element formed from said first and second similarly shaped parts.

4. The device of claim 3 wherein said independently overlapping means is a ferrule concentrically disposed about said catheter and urged into said bore to expand said parts into locking relationship with said ring.

5. The catheter assembly of claim 3 wherein said element is removable from the catheter by separating said first and second parts.

6. The catheter assembly of claim 3 wherein said independent means comprises a ferrule concentrically disposed about the catheter and wherein said ferrule is received in said bore between said brake means and said catheter.

7. In a catheter assembly having a protective sterile sleeve with a sealed end and an open end, a catheter disposed in said sleeve and adapted to be fed into a patient, a cannula for implantation in said patient, and an improved catheter feeder comprising:

a barrel-shaped element formed of a first and second half and having a bore therethrough for receiving the catheter;

separate pad means in said bore covering a portion of said catheter;

brake means in said element for selectively urging said pad means into engaging and disengaging contact with said catheter so that when said brake means is engaged, said catheter remains in a fixed position with respect to said barrel-shaped element, and when said brake means is disengaged, said catheter is able to pass freely through said bore;

said pad means comprises a ferrule concentrically disposed about the catheter and wherein said ferrule is received in said bore between said brake means and said catheter; and a ring is secured to the open end of the protective sanitary sleeve for receiving said barrel-shaped element so as to maintain said first and second halves together, and said ferrule is wedged into said bore to expand the halves into sealing relationship with said ring.

8. The catheter assembly of claim 7 wherein a protrusion extends from the barrel-shaped element, which protrusion is adapted to be received within the cannula.

9. The catheter assembly of claim 7 wherein said barrel-shaped element has an opening extending through one half of said element, said opening communicating with said bore, and
   said brake means includes a rod disposed within said opening and having an end adapted to engage the pad means and another end adapted to be manipulated digitally.

10. The catheter assembly of claim 7 wherein the first and second halves are of substantially identical shape.

11. A device for aiding in threading a catheter, comprising:
    an elongate cylindrically-shaped element having a distal end and a proximal end and having a bore therethrough for receiving a catheter;
    a distal end of said catheter extending from the distal end of said element;
    a tapered locking ferrule surrounding a portion of said catheter and extending into the proximal end of said element;
    a brake means carried by said element in transverse alignment with said catheter and with a distal portion of said ferrule for selectively engaging and disengaging said ferrule so that when said brake means is engaged said ferrule locks said catheter in a fixed position with respect to said element and when said brake means is disengaged said ferrule permits said catheter to pass freely in retrograde or prograde through said bore.

12. A device for aiding in threading a catheter, comprising:
    an elongate cylindrically-shaped element having a distal end and a proximal end and having a bore therethrough for receiving a catheter;
    a distal end of said catheter extending from the distal end of said element;
    a tapered locking ferrule surrounding a portion of said catheter and extending into the proximal end of said element;
    a brake means carried by said element in transverse alignment with said catheter and with a distal portion of said ferrule for selectively engaging and disengaging said ferrule so that when said brake means is engaged said ferrule locks said catheter in a fixed position with respect to said element and when said brake means is disengaged said ferrule permits said catheter to pass freely in retrograde or prograde through said bore;
    a sterile sleeve enclosing said catheter;
    a ring on one end of said sterile sleeve engaging the proximal end of said cylindrically-shaped element and said ferrule expanding said cylindrically-shaped element to engage said ring to seal said ring to said element.

13. In a catheter assembly having a protective sterile sleeve with a sealed end and an open end, a catheter disposed in said sleeve and adapted to be fed into a patient, a cannula for implantation in said patient, and an improved catheter feeder comprising:
    a barrel-shaped element having a distal end and a proximal end and having a bore therethrough for receiving the catheter;
    said open end of said sleeve seating on said proximal end of the barrel-shaped element with said distal end of the barrel-shaped element seated in said cannula;
    a ferrule surrounding a portion of said catheter and extending into the proximal end of said element;
    brake means in said element for selectively engaging and disengaging said ferrule so that when said brake means is engaged said ferrule will hold said catheter in a fixed position with respect to said barrel-shaped element and when said brake means is disengaged said ferrule will permit said catheter to pass freely through said bore.

14. In a catheter assembly as claimed in claim 13 wherein said barrel-shaped element is split along the longitudinal axis to provide two halves and wherein said open end of said sleeve has a rigid ring encircling the proximal ends of said halves to hold said halves together.

* * * * *